United States Patent [19]

Blough, Jr.

[11] Patent Number: 4,539,295

[45] Date of Patent: Sep. 3, 1985

[54] BINARY KINETIC ASSAY METHOD AND APPARATUS

[75] Inventor: William M. Blough, Jr., Fullerton, Calif.

[73] Assignee: Beckman Instruments, Inc., Fullerton, Calif.

[21] Appl. No.: 509,903

[22] Filed: Jun. 30, 1983

[51] Int. Cl.³ .................... G01N 21/77; G01N 33/00
[52] U.S. Cl. ........................................ 436/34; 422/68; 435/4; 436/164
[58] Field of Search .................. 436/34, 175, 517, 164; 422/68; 435/4, 17

[56] References Cited

U.S. PATENT DOCUMENTS

| | | | |
|---|---|---|---|
| 3,378,463 | 4/1968 | Guilbault et al. | 435/18 X |
| 3,682,586 | 8/1972 | Ertinghausen et al. | 23/230 |
| 3,857,771 | 12/1974 | Sternberg | 204/195 |
| 3,881,992 | 5/1975 | Ralston | 195/103.5 |
| 3,894,843 | 7/1975 | Jarvis | 23/230 |
| 3,915,644 | 10/1975 | Walraven | 436/34 |
| 3,989,383 | 11/1976 | Paulson | 356/96 |
| 4,111,657 | 9/1978 | Denney et al. | 23/230 |
| 4,289,498 | 9/1981 | Baughman et al. | 436/34 |
| 4,309,112 | 1/1982 | Ashley et al. | 356/436 |

OTHER PUBLICATIONS

Fabiny, D. L. and Ertingshausen, G., "Automated Reaction-Rate Method for Determination of Serum Creatinine with the CentrifiChem," Clinical Chemistry, vol. 17, No. 8, 1971, pp. 696–700.
Bowers, L. D., "Kinetic Serum Creatinine Assays I. The Role of Various Factors in Determining Specificity," Clinical Chemistry, vol. 26, No. 5, 1980, pp. 551–554.
Bowers, L. D. and Wong, E. T., "Kinetic Serum Creatinine Assays II. Critical Evaluation and Review," Clinical Chemistry, vol. 26, No. 5, 1980, pp. 555–561.

Primary Examiner—Barry S. Richman
Assistant Examiner—Robert J. Hill, Jr.
Attorney, Agent, or Firm—W. H. May; A. Grant; G. T. Hampson

[57] ABSTRACT

A kinetic assay method and apparatus for performing such method wherein a first sample containing predetermined concentrations of binary analytes is reacted with the reagent to form a reaction product. Reaction rates at first and second times are measured for the first reaction and a first ratio between such measured reaction rates is determined. A second reaction with a second sample and the reagent is also performed wherein the second sample contains predetermined concentrations of the binary analytes. Reaction rates at the first and second times are measured for the second reaction and a second ratio between such rates is determined. A third reaction with a third sample and the reagent is performed, the sample including unknown relative concentrations of the first and second analytes. Reaction rates are again measured at the first and second times and a third ratio between such measured reaction rates is determined.

By comparing the first and third ratios, an indication can be provided to show that the reaction is not influenced by an interfering analyte. The third ratio may be compared to a range of ratios defined by the first and second ratios to determine the relative contribution of at least one of the analytes to a reaction product formed during the third reaction. The relative contribution of a selected one of the analytes may be used to determine a concentration of such analyte corrected for the influence or bias of the other analyte in the reaction.

10 Claims, 4 Drawing Figures

BINARY KINETIC ASSAY METHOD AND APPARATUS

FIELD OF THE INVENTION

The present invention relates generally to the field of kinetic assay of analytes and more particularly to an improved method and apparatus for binary kinetic assays. In particular, the method and apparatus are suited for flagging the presence of two analytes in a sample, determining the relative contributions of two analytes to the total reaction occurring in a kinetic assay of such analytes, and determining a concentration of either of the analytes corrected for the bias of the other analyte in a binary kinetic assay.

BACKGROUND OF THE INVENTION

Kinetic methods of analysis are known for measuring concentrations of an analyte in a sample. Kinetic analyses are based on the principle that a reaction between the analyte to be measured and a suitable reagent need not be completed in order to determine the initial concentration of the analyte. Instead, the rate at which the reaction occurs, that is, at which a reaction product is formed, is measured at a preselected time after the start of the reaction. The rate of the reaction so determined is proportional to the initial concentration of the analyte and such concentration may be determined from a calibration curve which relates reaction rate to initial analyte concentration.

Two approaches to kinetic analysis are generally well known in the art. In each approach, a reaction product signal is developed which is proportional to the quantity of reaction product formed by an analyte and reagent in a sample. As the reaction progresses, the reaction product signal varies in accordance with the quantity of reaction product formed.

In a first type of kinetic analysis, sometimes referred to as two point or multipoint rate analysis, the reaction product signal is measured at two or more predetermined times or "points" after the beginning of the reaction. The reaction product signals measured over the time period covered by the predetermined times is analyzed to determine the slope of a line which best fits the measured reaction product signals. The slope is indicative of an average reaction rate during such time period. The average reaction rate so measured may then be compared to a calibration curve to determine the initial analyte concentration in the sample. Examples of apparatus employing two point or multipoint kinetic analysis techniques include the ABA-200 ® biochromatic analyzer from Abbott Laboratories, the Centrifichem ® System 400 from Union Carbide Corporation and the Cobas ® Bio from Roche Analytical Instruments.

A second approach to kinetic analysis, sometimes referred to as derivative analysis, may be performed electronically by differentiating the reaction product signal to form a rate signal which is proportional to the rate of change of the quantity of reaction product formed during the reaction. The rate signal is measured at a predetermined time after the start of a reaction and may be compared to a calibration curve to relate the differentiated reaction rate signal to an initial analyte concentration. The ASTRA ™ Automated Stat/Routine Analyzer System manufactured by Beckman Instruments, Inc. includes modules which perform kinetic analysis using such a derivative technique.

Kinetic analysis methods have been widely used for in vitro quantitation of creatinine to estimate total renal function. A reaction known as the Jaffe reaction has been the method of choice for such analysis and refers to a reaction of creatinine with picric acid in an alkaline medium to form a red colored creatinine-picric acid complex. Using the Jaffe reaction, it is possible to assess the function of the kidney with a creatinine clearance test that measures the relative amount of creatinine excreted in the urine with respect to the serum creatinine concentration. The creatinine clearance test provides a more sensitive indication of renal function than quantitation of serum or urine creatinine alone.

Unfortunately, the Jaffe reaction is not specific to creatinine, that is, the Jaffe reaction performed in the presence of one or more interfering substances or "interferents" may result in a positive or negative bias in the Jaffe reaction product. Although a number of substances have been identified which produce a bias in the Jaffe reaction result, it has been recognized for some time that acetoacetate is the most frequent analytical interferent in creatinine kinetic assays where the reaction rate is measured at a time when interferents having reaction rates generally faster than creatinine are still contributing significantly to the reaction product. Acetoacetate interference produces a positive bias in the Jaffe reaction product. Various disturbances in normal metabolism may produce levels of acetoacetate in patient serum which may substantially effect the accuracy of a creatinine clearance test. In view of the importance of determining creatinine concentration in estimating total renal function, it is clear that creatinine levels should be measured so as to minimize or eliminate acetoacetate interference.

Prior kinetic analytical methods have attempted to minimize acetoacetate interference in creatinine assays by delaying the measurement of the reaction rate to a time at which the contribution of acetoacetate to the formation of the reaction product is small as compared to the amount of reaction product formed by creatinine. Such a method is disclosed in U.S. Pat. No. 3,682,586 to Ertingshausen et al. for "Process for the Determination of Creatinine Body Fluids". However, such methods merely reduce acetoacetate interference in the creatinine determination and do not indicate that acetoacetate bias may be present in the measured reaction rate. The prior methods also do not compensate or correct the measured reaction rate and resulting creatinine concentration for acetoacetate interference. Furthermore, the delay required before reading the reaction rate reduces the number of assays which may be performed and thus the throughput of the kinetic assay apparatus. Moreover, delaying the measurement of the reaction rate requires that the reaction rate be measured after a significant portion of creatinine has already reacted with the Jaffe reaction reagent, decreasing the sensitivity and/or accuracy of the kinetic assay.

Thus, there is a need for a method and apparatus for the kinetic assay of creatinine which indicates that the result of the assay is influenced by the presence of acetoacetate. There is also a need for a kinetic assay method and apparatus which corrects for the influence of acetoacetate in determining creatinine concentration. There is a further need to provide a kinetic assay method and apparatus which relatively rapidly performs creatinine kinetic assays while correcting for the influence of acetoacetate in creatinine concentration determinations. Furthermore, there is a need for a creatinine kinetic assay method and apparatus which measures reaction rate while a significant concentration of creatinine remains in the sample undergoing analysis to thereby improve the sensitivity and/or accuracy of the creatinine concentration determination.

SUMMARY OF THE INVENTION

A method and apparatus in accordance with the present invention overcomes the limitations and drawbacks described above and enables the determination of the relative contributions of two analytes to a reaction product. Moreover, the concentration of either of such analytes corrected for the bias introduced by the other of such analytes, may be determined. Advantageously, the method and apparatus of the present invention may be used to provide a simple and reliable means for flagging kinetic assay results which may be biased by interferents.

Toward the foregoing ends, a kinetic assay method and apparatus in accordance with the present invention performs a first reaction with a first sample and a reagent. The first sample contains predetermined concentrations of binary analytes, both of which react with the reagent to form a reaction product. The predetermined concentrations of the binary analytes produce known relative contributions to the reaction product formed in the first reaction. During the first reaction, the reaction rate is measured at first and second times after the start of the reaction and a first rate ratio is determined between the two measured reaction rates.

A second reaction with a second sample and the reagent is also performed. The second sample contains different predetermined concentrations of the binary analytes which also produce known relative contributions to the reaction product. Reaction rates for the second reaction are measured at the same first and second times after the start of the second reaction. A second ratio between such rates is determined.

A third reaction with a third sample and the reagent is performed, the sample including unknown relative concentrations of the first and second analytes. Reaction rates are again measured at the first and second times after the start of the third reaction and a third ratio between such measured reaction rates is determined.

By comparing the first and third ratios, an indication can be provided to show that the reaction is or is not influenced by an interfering analyte. The third ratio may be compared to a range of ratios defined by the first and second ratios to determine the relative contribution of at least one of the analytes to the reaction rates measured at the first and second times. The relative contribution of at least one analyte may be used to determine a concentration of such analyte corrected for the influence or bias of the other analyte in the reaction.

Preferably, the first and second times are selected to be substantially at or between reaction rate peak times for reactions involving pure analytes and the reagent. The first and second samples may comprise pure solutions of the first and second analytes, respectively, thereby directly defining a range of reaction rate ratios to be expected in performing reactions of solutions having unknown concentrations of the two analytes.

In the embodiment disclosed herein, the first analyte may be creatinine and the second analyte may be acetoacetate. However, the method and apparatus of the present invention are equally adaptable to other binary assay systems where the binary analytes have differing reaction rates.

DETAILED DESCRIPTION OF THE INVENTION

Figure 1:
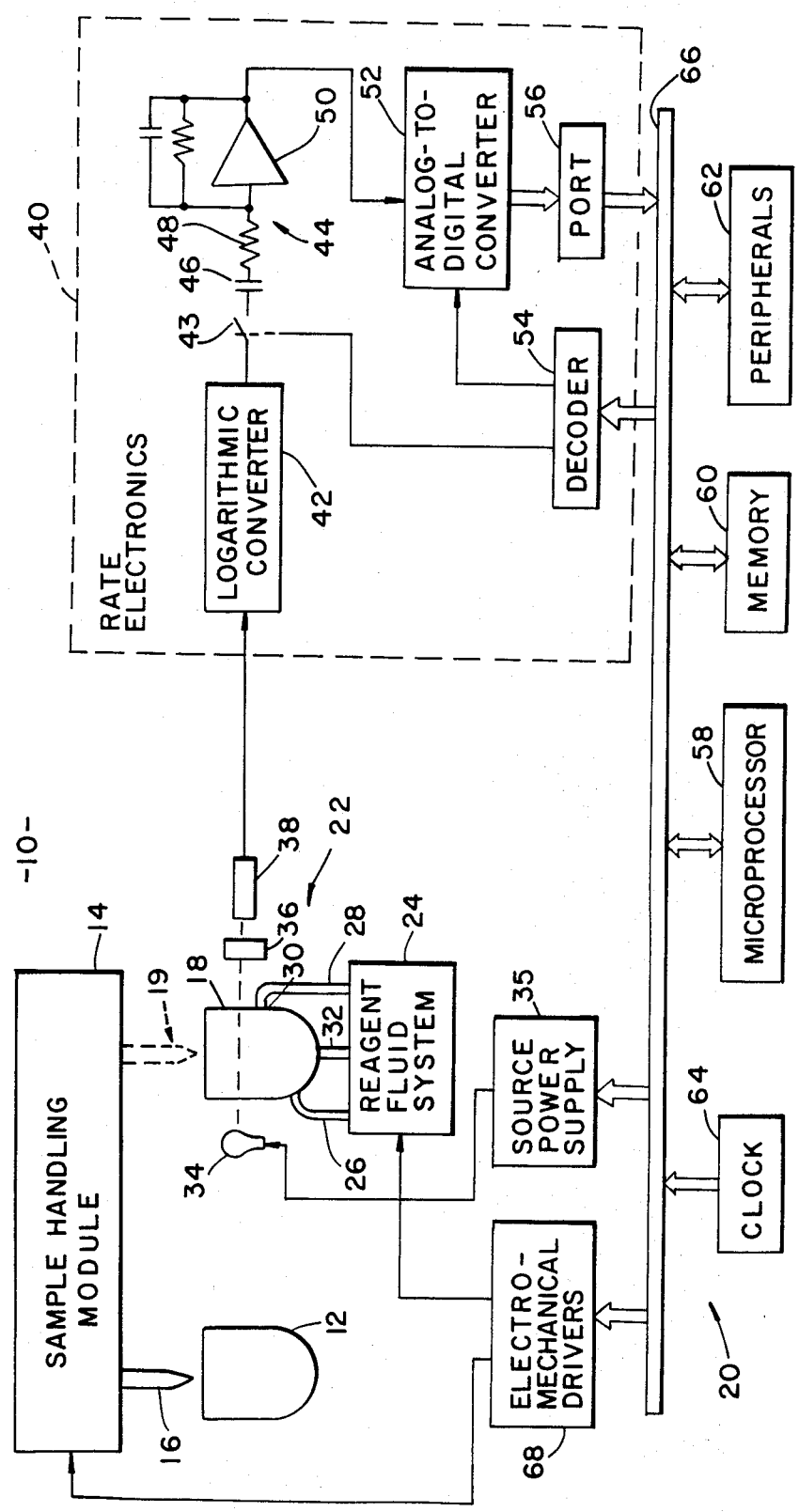
FIG. 1 is a block diagram of an apparatus in accordance with the present invention.

With reference to FIG. 1, a kinetic or rate assay apparatus 10 in accordance with the present invention includes a sample cup 12 adapted to hold a quantity of sample to be analyzed. A sample handling module 14 of conventional design includes a probe 16 which is adapted to draw and hold a predetermined volume of sample from the sample cup 12 and deliver a portion thereof to a reaction cup 18. In so delivering the sample to the reaction cup 18, the probe 16 is moved by the sample handling of module 14 to a second position 19 indicated in phantom above the reaction cup 18. As will be described below, the sample handling module 14 as well as other elements of the apparatus 10 are controlled by means of a control computer 20.

The reaction cup 18 is part of a reaction station 22 where the reaction between the sample and a reagent is performed. The reaction station 22 includes a reagent fluid system 24 which delivers predetermined volumes of reagent to the reaction cup 18. In particular, the reagent fluid system 24 includes a fill conduit 26 through which flows reagent so as to fill the reaction cup 18. A sip conduit 28 is in communication with the reaction cup 18 through a port 30 at a predetermined level within the reaction cup 18. Once the reaction cup 18 has been filled with reagent, reagent may be drawn through the sip conduit 28 to a level determined by the sip port 30 to accurately adjust the volume of reagent in the reaction cup 18. The reaction cup 18 may be drained by means of a drain conduit 32. The reagent fluid system 24 includes a plurality of paristaltic pumps controlled by the control computer 20 to perform the fill, sip and drain functions just described.

The reaction station 22 further includes a light source 34 positioned to transmit light through the reaction cup 18. The light source 34 receives power from a suitable source power supply 35 controllable by means of the control computer 20 so as to turn on or off the light source 34. The light transmitted through the reaction cup 18 is directed through an interference filter 36 and is detected by a suitable detector 38 such as a photodiode or a photomultiplier tube. Preferably, the reaction station 22 includes means (not shown) for maintaining the temperature of the reagent cup 18 and the solution contained therein at about 36° C. to 38° C.

With continued reference to FIG. 1, the output of the detector 38 is applied to rate electronics 40. The rate electronics 40 includes a logarithmic converter 42 of conventional design. The output of the logarithmic converter 42 is applied through a switch 43 to a differentiating circuit 44 including a differentiating capacitor 46, resistor 48 and amplifier 50. The differentiating circuit 44 provides a rate signal output representing the first derivative of the signal from the logarithmic converter 42. In the embodiment disclosed herein, the time constant of the differentiating circuit 44 is about 4.6 seconds.

The rate signal at the output of the differentiating circuit 44 is applied to an analog-to-digital converter (ADC) 52. The ADC 52 is controlled via a decoder 54 responsive to the control computer 20 to convert the differentiator output signal into a binary representation thereof which is applied through a port 56 to the control computer 20. The decoder 54 also controls the switch 43.

The control computer 20 includes a microprocessor 58, memory 60, peripherals 62, and a real time clock 64, all in communication with a bus 66. The bus 66 is further in communication with the source power supply 35, the decoder 54 and the port 56. The control computer system is of conventional design and may use, for example, a type 8080A microprocessor from Intel. Such control computer systems 20 are well known to the art. The bus 66 is also connected to electromechanical drivers 68 which in turn drive electromechanical components such as pumps and stepper motors within the sample handling module 14 and the reagent fluid system 24.

As will be apparent to those skilled in the art, the apparatus 10 of FIG. 1 is essentially a conventional kinetic or rate assay instrument modified in accordance with the teachings set forth herein. Such modifications may include, for example, modified or new software stored in the memory 60 which, in effect, reconfigures the elements as taught herein. For example, a conventional instrument suitable for modification is an ASTRA TM Stat/Routine Analyzer manufactured by Beckman Instruments, Inc., including a creatinine chemistry module. Those skilled in the art will recognize that other instruments may be designed in accordance with the teachings herein. Such instruments generally employ sample handling modules, reagent fluid systems, electronic circuits and control techniques well known in the art. Moreover, although an automated apparatus 10 has been described in FIG. 1, it will be recognized that considerably more simplified apparatus including, for example, manual sample and reagent handling are all adaptable for use with the present invention.

The operation of the apparatus 10 will be described for determining the concentration of creatinine in a sample also containing an unknown concentration of acetoacetate using a Jaffe reaction reagent. Generally, the apparatus 10 performs kinetic rate analyses for a sample containing pure creatinine, a sample containing pure acetoacetate, and a sample containing unknown concentrations of creatinine and acetoacetate. For each kinetic rate analysis performed, the rate electronics 40 provide a measurement of the reaction rate at two predetermined times after the reaction begins. Advantageously, by determining the reaction rates at two times for each reaction, the ratio of such reaction rates for the sample containing unknown concentrations of creatinine and acetoacetate may be compared to the similar ratio obtained from a sample containing pure creatinine. The comparison provides an indication of whether the reaction rate for the sample with unknown concentrations is influenced by the presence of interferents. Further, a comparison of the unknown sample ratio to similar ratios for samples containing pure creatinine and pure acetoacetate provides an indication of the contribution of creatinine and acetoacetate to the reaction product. Moreover, such a comparsion enables a determination of creatinine concentration to be corrected for the influence or bias of acetoacetate.

With reference to FIG. 1, the operation of the apparatus 10 begins by performing a kinetic rate analysis of a sample containing pure creatinine and no other Jaffe reaction component. The microprocessor 58 controls the source power supply 35 to turn on the light source 34 throughout the operation of the apparatus 10. With the light source 34 energized, the detector 38 detects light passing through the reaction cup 18 and the interference filter 36. The microprocessor 58 also controls the decoder 54 so as to open the switch 43. The sample handling module 14 is controlled via the electromechanical drivers 68 to draw a predetermined volume of the sample from the sample cup 12 into the probe 16. The microprocessor 58 then controls the sample handling module 14 to move the probe 16 to the position 19 above the reaction cup 18. Concurrently, the microprocessor 58 controls the Jaffe reaction reagent fluid system 24 to fill the reagent cup 18 with reagent to a level determined by the sip port 30.

With the reagent in the reaction cup 30, the sample handling module 14 is controlled so as to inject a precisely determined volume of sample from the probe 16 into the cup 18. At the time of injection, the microprocessor 58 begins a timing function implemented by the microprocessor 58 in a conventional fashion as by "counting down" a register or memory 60 address at predetermined time intervals. The timing function is used to time the reaction occurring in the reaction cup 18.

At some predetermined time after the reaction has begun, the microprocessor 58 controls the decoder 54 to close the switch 43. In the embodiment disclosed herein, the switch 43 is closed nine seconds after the reaction has begun.

The reaction product formed in the sample absorbs light within the narrow wavelength bandpass range of the interference filter 36. In the embodiment disclosed herein, the bandpass range is centered at about 520 nm. As the reaction product forms, less light reaches the detector 38, varying the output thereof. The logarithmic converter 42 converts the output of the detector 38 into a signal which is proportional to the absorbance, and thus the concentration, of the reaction product formed in the reaction cup 18. With the switch 43 closed, the output of the differentiating circuit 44 is consequently a signal which is proportional to the rate of change of the formation of reaction product within the cup 18, that is to say, it is proportional to the reaction rate. As seen with reference to FIG. 2, the output of the differentiating circuit 44 describes a creatinine rate curve 70 wich begins nine seconds after the reaction begins. The nine second delay in closing the switch 43 allows fast reacting interferents in the sample to complete their reaction before the differentiating circuit 44 begins to generate a reaction rate signal. As will be appreciated by those skilled in the art, the differentiating circuit 44 requires a settling time related to the time constant of the circuit 44 before the curve 70 accurately represents the reaction rate occurring in the sample cup 18.

Figure 2:
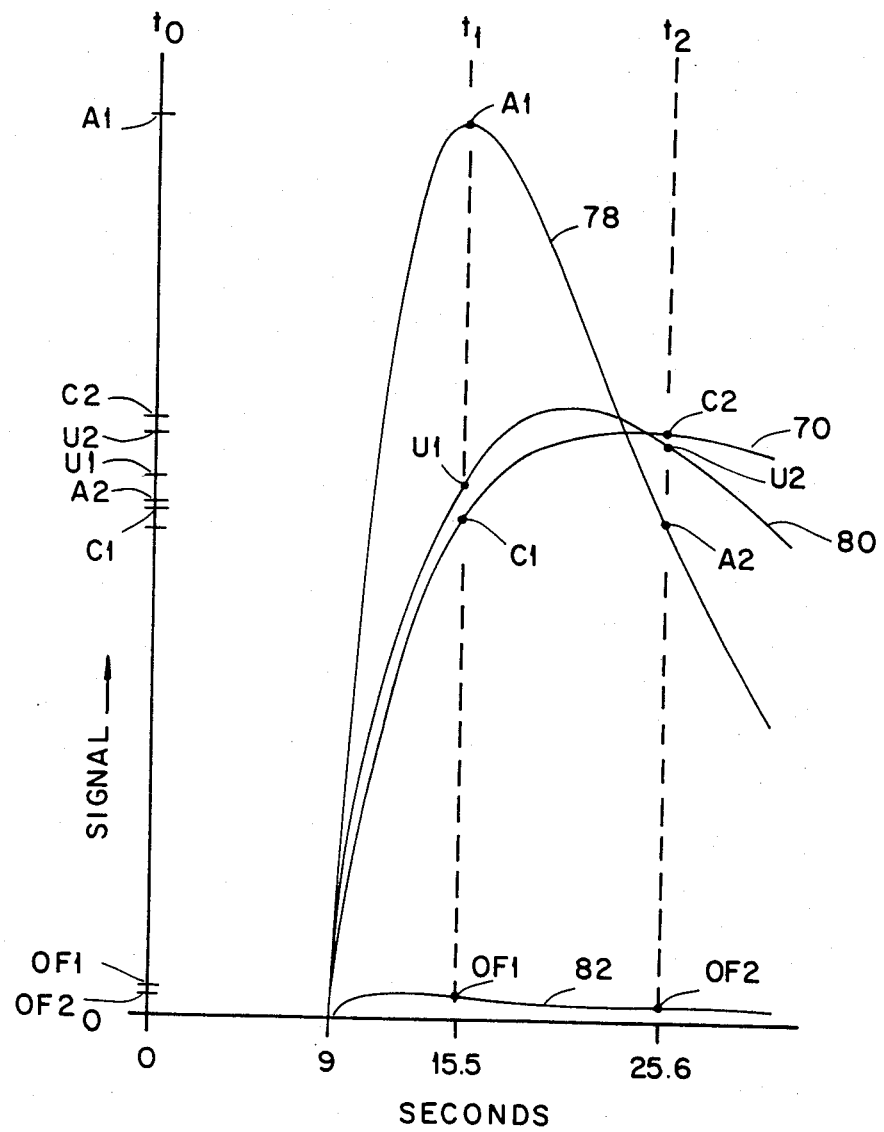
FIG. 2 depicts a set of reaction rate curves and rate signal value points measured by the apparatus of FIG. 1.

The microprocessor 58 through the decoder 54 controls the ADC 52 to convert the output of the differentiating circuit 44 into a digital representation. The digital representation is read by the microprocessor 58 through the port 56 and may be stored into the memory 60 in a conventional fashion. In accordance with the present invention, the output from the differentiating circuit 44 is converted into two digital representations at two predetermined times $t_1$ and $t_2$. In the embodiment disclosed herein the first and second predetermined times $t_1$ and $t_2$ are 15.5 seconds and 25.6 seconds, respectively, after the start of the reaction. The time $t_2$ is selected to be at or slightly before the peak in the creatinine rate curve 70. The time $t_1$ is selected as described below. As seen in FIG. 2, the digital representation generated by the ADC 52 at $t_1$ represents a signal value C1 and the digital representation generated at $t_2$ represents a signal level C2, both corresponding to reaction rates at the times $t_1$ and $t_2$.

Similarly, the apparatus 10 performs a kinetic rate analysis of a sample of pure acetoacetate, that is, only acetoacetate contributes to the reaction product. The acetoacetate sample produces a differentiator output signal represented by an acetoacetate curve 78 in FIG. 2. The ADC 52 is controlled to generate digital output values A1 and A2 at times $t_1$ and $t_2$, respectively, corresponding to rate signal values at such times. Again, the digital output values A1 and A2 may be stored by the microprocessor 58 in the memory 60. The time $t_1$ is selected to be at or slightly after the peak in the acetoacetate rate curve 78. The predetermined times $t_1$ and $t_2$ are selected to be at or between the peaks of the rate curves 70 and 78 to maximize the accuracy of the results obtained with the present invention and to eliminate the possibility of ambiguous digital output values which could otherwise result for times selected to be on either side of the peaks of the curves 70 and 78.

The apparatus 10 also performs a kinetic rate analysis for a sample containing unknown concentrations of creatinine and acetoacetate. With reference to FIG. 2, the sample produces an output from the differentiating circuit 44 corresponding to a curve 80. At times $t_1$ and $t_2$ the microprocessor 58 controls the ACD 52 to determine digital output values U1 and U2, each representing respective signal levels at the output of the differentiating circuit 44 at times $t_1$ and $t_2$. The digital output values U1 and U2 are stored by the microprocessor 58 into the memory 60.

The digital output values obtained as just described must be corrected for signal offsets present in the rate measurement process. The signal offsets may arise because of the "blank rates" in the reagent, that is, rates detectable in the absence of an analyte, or may be generated by offsets in the rate electronics 40. The signal offset values may be obtained by operating the apparatus 10 to analyze a sample which is not reactive with the reagent, producing an output at the differentiating circuit 44 represented by an offset rate curve 82 in FIG. 2. Offset digital output values OF1 and OF2 determined at the times $t_1$ and $t_2$ are also stored by the microprocessor 58 into the memory 60. The offsets may also be obtained mathematically with respect to a calibration curve by calculating the offset present with a zero concentration analyte.

With the digital output values obtained as just described, the microprocessor 58 may be operated to determine rate ratios for each of the pairs of digital output values obtained. In doing so, the microprocessor 58 first determines a creatinine rate ratio $C_r$, an acetoacetate rate ratio $A_r$, and an unknown rate ratio $U_r$ according to the following relationships:

$$C_r = \frac{C1 - OF1}{C2 - OF2} \quad \text{Equation 1}$$

$$A_r = \frac{A1 - OF1}{A2 - OF2} \quad \text{Equation 2}$$

$$U_r = \frac{U1 - OF1}{U2 - OF2} \quad \text{Equation 3}$$

In accordance with one aspect of the present invention, the $C_r$ and $U_r$ rate ratios so determined may be used for the identification, detection or flagging of reactions which appear to contain analytes other than creatinine. With reference to FIG. 2 and equation 1, the rate ratio $C_r$ for a pure solution of creatinine obtained from the curve 70 by equation 1 represents a rate ratio to be expected when the only Jaffe reactant in a sample is creatinine. If the sample contains an interferent such as acetoacetate having a reaction rate peak differing in time from the peak for the pure creatinine curve 70, that is, time $t_2$, the the reaction rate ratio $U_r$ for the unknown sample in accordance with equation 3 will vary from the ratio $C_r$.

For example, as seen in FIG. 2, the unknown sample curve 80 yields values U1 and U2 which result in an unknown reaction rate ratio $U_r$ in accordance with equation 3 which is not equal to the creatinine ratio $C_r$. By comparing the unknown reaction rate ratio $U_r$ to the creatinine rate ratio $C_r$, the presence of an interferent or interferents in the unknown sample is indicated. In the embodiment disclosed herein, the comparison is performed by the microprocessor 58 in a conventional fashion.

Preferably, the creatinine rate ratio $C_r$ will define one point within an acceptable range of unknown rate ratio, within which the unknown sample will be assumed to include relatively insignificant concentrations of interferents. For example, such a range may be $C_r$ plus or minus ten percent of the absolute value of the difference between $A_r$ and $C_r$, that is $C_r \pm 0.10 \, (|A_r - C_r|)$, particularly if the apparent or uncorrected creatinine concentration determined as is described herein below, is greater than about 10 mg/dl. If $U_r$ is outside such a ratio range or window, the microprocessor 58 would advise the user of the apparatus 10 via the peripherals 62 that the unknown sample may include unacceptable concentrations of interferents. Conversely, the microprocessor 58 may advise the user if the rate ratio $U_r$ is within an acceptable range defined with respect to the ratio $C_r$.

Figure 3:
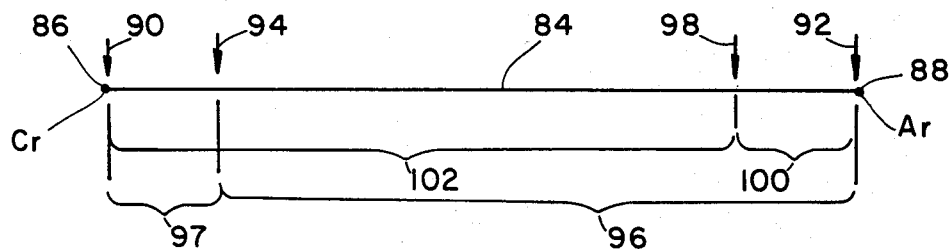
FIG. 3 depicts a rate ratio line segment useful in describing the concepts of the present invention.

In accordance with another aspect of the present invention, the microprocessor 58 compares the unknown rate ratio $U_r$ to the creatinine and acetoacetate rate ratios $C_r$ and $A_r$ to determine the relative contributions of each analyte to the total reaction product. Such a comparison may be represented diagramatically with reference to FIG. 3. A line segment 84 represents a range of ratios between an endpoint 86 corresponding to the creatinine rate ratio $C_r$ and an endpoint 88 corresponding to the acetoacetate rate ratio $A_r$. If a rate ratio $U_r$ for a sample containing unknown concentrations of creatinine and acetoacetate falls at the endpoint 86 as depicted by arrow 90 then only creatinine contributes to the reaction product. Conversely, an unknown sample reaction rate ratio $U_r$ falling at the endpoint 88 as depicted by arrow 92 indicates that only acetoacetate contributes to the reaction product formed during the unknown sample reaction performed by the apparatus 10.

However, if the sample rate ratio $U_r$ falls near the endpoint 86 as depicted by arrow 94, then creatinine contributes to the reaction product by an amount proportional to a ratio formed between the length of a line segment 96 between the endpoint 88 and the arrow 94 to the length of a rate ratio range line segment 84 as defined by the endpoints 86 and 88. The contribution of acetoacetate to the reaction product is proportional to the length of a line segment 97 between the endpoint 86 and the arrow 94 to the length of the line segment 84. Similarly, a sample having a rate ratio $U_r$ depicted by an arrow 98 also includes both creatinine and acetoacetate. The portion of the reaction product formed by creatinine is proportional to a ratio formed by the length of a line segment 100 between the endpoint 88 and the arrow 98 to the rate ratio range line segment 84. Similarly, the portion of the reaction product formed by acetoacetate is proportional to the length of a line segment 102 defined by the end-point 86 and the arrow 98 to the length of the rate ratio range line segment 84.

Thus, the rate ratios for samples of pure creatinine and acetoacetate establish a rate ratio relationship which may be used to determine the relative contributions of creatinine and acetoacetate to a reaction product in a sample according to the rate ratio of the sample. The examples discussed above in FIG. 3 may be expressed more compactly and in a more general form as follows:

$$UC = \frac{U_r - A_r}{C_r - A_r} \qquad \text{Equation 4}$$

$$UA = \frac{U_r - C_r}{A_r - C_r} \qquad \text{Equation 5}$$

where UC is a value in the range of 0 to 1 equal to the portion of the reaction product contributed by creatinine and UA is a value in the range of 0 to 1 equal to the portion of the reaction product contributed by acetoacetate.

Figure 4:
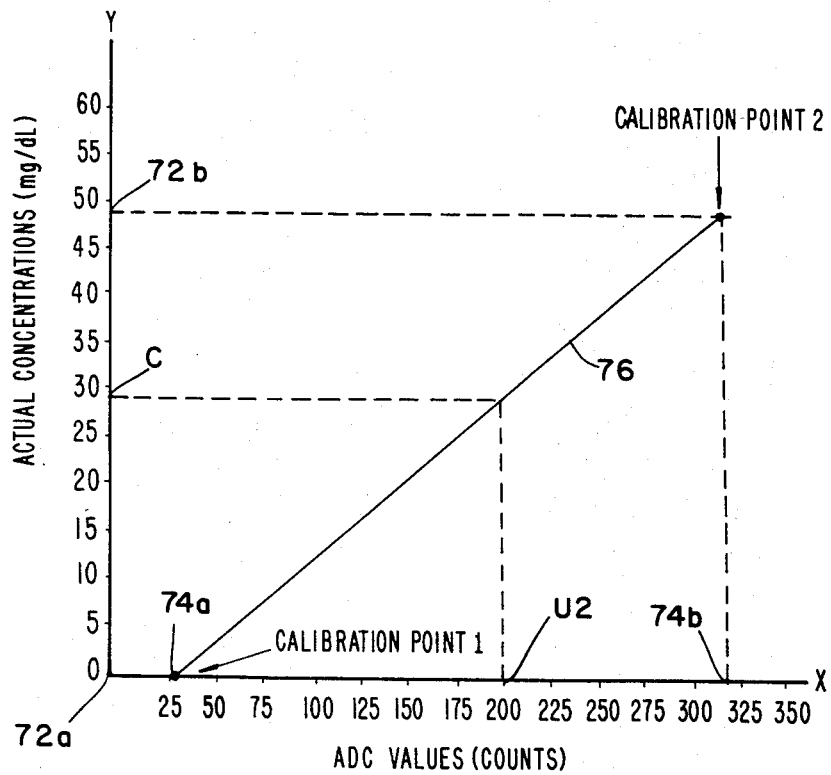
FIG. 4 is an example of a conventional calibration curve useful with one embodiment of the present invention.

In a third aspect of the present invention, the rate ratios described above may be used by the microprocessor 58 to determine creatinine concentration in a sample corrected for the influence or bias of acetoacetate. An uncorrected creatinine concentration C is first determined in a conventional fashion. For example, the digital representation of the signal level U2 may be compared to a calibration curve as shown in FIG. 4. Such a calibration curve is determined in a conventional fashion by analyzing two samples having known concentrations 72a and 72b of creatinine to determine ADC digital values 74a and 74b, each at time $t_2$. The known creatinine concentrations 72a and 72b are then related to the ADC digital values 74a and 74b to define a calibration curve 76. The U2 ADC digital output obtained at the time $t_2$ is then compared to the calibration curve 76 to determine creatinine calibration C.

However, such creatinine concentration assumes that only pure creatinine is contributing to the reaction product. In the example described here, the sample contains unknown concentrations of both creatinine and acetoacetate and thus the creatinine concentration determined from the calibration curve 76 may include an error due to the positive bias of acetoacetate in forming the reaction product.

Having determined UC in accordance with equation 4 above a corrected creatinine concentration UCC may be determined from the uncorrected concentration value C and the creatinine contribution value UC as follows:

$$UCC = C \times UC \qquad \text{Equation 6}$$

Table 1 sets forth several examples of kinetic rate analyses of creatinine using the present invention. The columns labeled "Sample" list the actual creatinine and acetoacetate concentrations in each sample. The samples were formulated using stock creatinine and acetoacetate solutions. The examples of Table 1 were performed on an ASTRA analyzer from Beckman Instruments, Inc. which includes a creatinine module and which is modified in accordance with the present invention. The reagent is a conventional Jaffe reaction reagent comprising 1600 mL of 0.188M sodium hydroxide solution buffered with sodium borate and sodium phosphate, mixed with 400 mL of 0.05M picric acid such as is available from Beckman Instruments, part number 668306.

In Table 1, the columns are labeled with the results obtained from equations 3, 4 and 6 above. As can be seen, the corrected creatinine concentration UCC is generally a more accurate representation of true creatinine concentration than the uncorrected creatinine concentration value C. Examples where UC=1 yet C does not equal UCC are attributed to round-off errors in the manipulations performed by the microprocessor 58. Also, in those examples where C is less than the values in the CREAT column, the lower C value results from calibration errors and such errors are not believed to be clinically significant. However, in the embodiment disclosed herein, UC is set equal to one when $U_r$ is less than $C_r$ and is set to zero when $U_r$ is greater than $A_r$. Such instances may result from noise in measurements involving very low signal levels with a relatively high proportional influence of OF1 and OF2.

As a specific example of measured values which produce the results shown in Table I, for the row in Table I with ACETO=10.0 and CREAT=50, U1=449.5, U2=362.0, OF1=19.0 and OF2=15.0. The values for $C_r$ and $A_r$ may be read directly from the entries in the $U_r$ column for the second and third rows where ACETO=0.0, CREAT=50, and ACETO=10, CREAT=0, respectively, or could have been determined as described above with reference to Equations 1 and 2.

Advantageously, the apparatus and method the present invention may also be used to quantitate acetoacetate concentration in the unknown sample. Using a calibration curve for acetoacetate similar to the curve of FIG. 4, an uncorrected acetoacetate concentration value A may be obtained from, for example, the rate U2 in FIG. 2. As with creatinine as described above, the unknown rate ratio $U_r$ is determined in accordance with equation 3 and the acetoacetate contribution value UA is then found in accordance with equation 5. An acetoacetate concentration UAA corrected for the influence of creatinine may be found as follows:

$$UAA = A \times UA \qquad \text{Equation 7}$$

Although the above example employs the rate U2 to determine the uncorrected acetoacetate concentration A, such concentration may be determined using an appropriate acetoacetate concentration curve from the rate U1 measured at time $t_1$. By doing so, the accuracy of the uncorrected concentration is improved because the time $t_1$ is selected to correspond to the peak in the acetoacetate rate curve 78. This it is seen that the apparatus and method of the present invention may easily quantitate two analytes in a sample.

Further, it will be recognized that the present method and apparatus may be used with other binary analyte systems wherein the binary analytes exhibit differing peak reaction rate times. As one example, Table II sets forth results obtained from applying the present invention to samples containing creatinine and cephalosporin. As with the binary system of creatinine and acetoacetate, samples containing pure solutions of creatinine and cephalosporin exhibit rate curves having differing peak times similar to the creatinine/acetoacetate system of FIG. 2. Thus, curves for pure solutions of creatinine and cephalosporin similar to the curves 78 and 80 may be determined. Equations similar to equations 1-4 may be used to determine the contribution of creatinine to the reaction product UC. In equations 2 and 4, the digital output values A1 and A2 and the ratio $A_r$ would be for cephalosporin rather than acetoacetate. In the examples of Table II, Keflin brand cephalosporin manufactured by Eli Lilly & Co. was used in creating the sample concentrations listed in the "Sample" column.

Although the flagging aspect of the present invention is useful for samples containing one analyte alone or the analyte with one or more interferents, it is assumed in performing the examples of Tables I and II above that the samples contain only the binary analytes creatinine/acetoacetate or creatinine/cephalosporin and no or insignificant amounts of other reactants which may bias the Jaffe reaction product. In a creatinine/acetoacetate system, for example, the user may wish to verify that acetoacetate is the predominant interferent. To do so, the concentration of acetoacetate determined in accordance with equation 7 may be compared to a quantitation of acetoacetate using a suitable reagent test strip such as reagent test strips for urinalysis marketed by the AMES Division of Miles Laboratories under the trademark Ketostix. If the concentrations are substantially identical, then acetoacetate may be assumed to be the interferent.

Various modifications to the present invention which do not depart from the scope of the apendent claims will be apparent to those skilled in the art. For example, although the invention has been described using pure analytes to obtain curves such as the curves 78 and 80 in FIG. 2, the present invention may be performed using two calibration solutions each containing known relative concentrations of the analytes. In such an instance, the endpoints 86 and 88 of the rate ratio range illustrated by the line segment 84 of FIG. 4 would be obtained by extrapolating the rate ratios obtained for the known solutions. Preferably, in such an embodiment the relative sensitivity of the apparatus 10 to the two analytes in the binary system would be constant or known in order to provide better resolution along the line segment 84 for unknown rate ratios $U_r$.

Moreover, although the embodiments disclosed herein have used a derivative technique analyzer, the present invention may also be used with two-point or multipoint analyzers by providing two two-point or multipoint determinations at or near the reaction rate curve peaks for the two analytes.

Also, although the invention has been described with respect to the rate of formation of a reaction product, the invention is applicable to kinetic rate analysis generally, including the analyses measuring the rate at which a reaction component may be consumed as with, for example, glucose determinations measuring the rate of disappearance of dissolved oxygen.

While a preferred embodiment of the present invention has been illustrated and described, it will be understood that various modifications may be made therein without departing from the subject and scope of the appended claims.

TABLE I

| Sample | | | | | |
|---|---|---|---|---|---|
| ACETO mmol/L | CREAT mg/L | C | $U_r$ | UC | UCC |
| 0.0 | 0 | 0 | 0.0000 | 1.0000 | 0.0 |
| 0.0 | 50 | 50 | 0.8230 | 1.0000 | 50.0 |
| 10.0 | 0 | 32 | 1.8659 | 0.0000 | 0.0 |
| 0.0 | 300 | OIR | 0.8224 | 1.0000 | 296.4 |
| 0.0 | 200 | 198 | 0.8216 | 1.0000 | 197.8 |
| 0.0 | 100 | 101 | 0.8189 | 1.0000 | 100.9 |
| 0.0 | 50 | 51 | 0.8280 | 0.9952 | 49.9 |
| 0.0 | 20 | 21 | 0.8068 | 1.0000 | 20.2 |
| 0.0 | 10 | 11 | 0.7978 | 1.0000 | 10.2 |
| 0.0 | 5 | 5 | 0.7609 | 1.0000 | 5.3 |
| 20.0 | 0 | 62 | 1.8963 | 0.0000 | 0.0 |
| 5.0 | 0 | 16 | 1.8971 | 0.0000 | 0.0 |
| 2.5 | 0 | 8 | 1.9265 | 0.0000 | 0.0 |
| 1.25 | 0 | 3 | 1.8750 | 0.0000 | 0.0 |
| 0.625 | 0 | 2 | 1.6875 | 0.1711 | 0.3 |
| 0.0 | 200 | 198 | 0.8188 | 1.0000 | 197.9 |
| 10.0 | 200 | 224 | 0.9656 | 0.8632 | 193.5 |
| 5.0 | 200 | 212 | 0.8973 | 0.9287 | 196.5 |
| 2.5 | 200 | 201 | 0.8621 | 0.9625 | 193.4 |
| 1.25 | 200 | 195 | 0.8423 | 0.9815 | 191.0 |
| 0.625 | 200 | 194 | 0.8337 | 0.9897 | 192.3 |
| 0.0 | 100 | 101 | 0.8204 | 1.0000 | 100.5 |
| 10.0 | 50 | 80 | 1.2406 | 0.5996 | 47.8 |
| 5.0 | 50 | 65 | 1.0762 | 0.7572 | 49.1 |
| 2.5 | 50 | 57 | 0.9574 | 0.8711 | 49.4 |
| 1.25 | 50 | 54 | 0.8968 | 0.9293 | 49.7 |
| 0.625 | 50 | 52 | 0.8575 | 0.9669 | 49.9 |
| 0.0 | 20 | 22 | 0.8492 | 0.9749 | 20.1 |
| 10.0 | 10 | 40 | 1.6243 | 0.2317 | 9.2 |
| 5.0 | 10 | 25 | 1.4679 | 0.3817 | 9.6 |
| 2.5 | 10 | 18 | 1.2745 | 0.5671 | 10.0 |
| 1.25 | 10 | 15 | 1.0400 | 0.7919 | 11.4 |
| 0.625 | 10 | 12 | 0.9804 | 0.8491 | 10.0 |

TABLE II

| Sample | | | | | |
|---|---|---|---|---|---|
| KEFLIN mg/L | CREAT mg/L | C | $U_r$ | $U_c$ | UCC |
| 0 | 0 | 0 | 0.0000 | 1.0000 | 0.0 |
| 0 | 50 | 50 | 0.9222 | 1.0000 | 50.0 |
| 1000 | 0 | 35 | 1.3562 | 0.0000 | 0.0 |
| 200 | 0 | 7 | 1.3793 | 0.0000 | 0.0 |
| 100 | 0 | 3 | 1.3103 | 0.1057 | 0.4 |
| 10 | 0 | 0 | 1.3103 | 0.1057 | —0.0 |
| 500 | 25 | 42 | 1.0872 | 0.6198 | 26.0 |
| 100 | 25 | 28 | 0.9713 | 0.8868 | 24.8 |
| 50 | 25 | 26 | 0.9520 | 0.9314 | 24.4 |
| 5 | 25 | 25 | 0.9213 | 1.0000 | 24.7 |
| 0 | 50 | 49 | 0.9095 | 1.0000 | 49.3 |
| 0 | 25 | 25 | 0.9163 | 1.0000 | 24.6 |
| 0 | 0 | 0 | 0.9222 | 1.0000 | —0.3 |

What is claimed is:

1. A method for providing an indication that a reaction between a sample containing at least a first analyte and a reagent is influenced by the presence of at least a second analyte in the sample also reacting with the reagent but at a rate different from the first analyte comprising the steps of:

performing a first reaction with only the first analyte and the reagent, measuring first and second reaction rates at respective first and second times during the first reaction, and forming a first ratio between the first and second reaction rates;

performing a second reaction with the sample and the reagent, measuring third and fourth reaction rates at the first and second times, respectively, during the second reaction, and forming a second ratio between the third and fourth reaction rates; and comparing the first ratio and the second ratio and providing the indication if the second ratio is in a predetermined relationship with the first ratio.

2. A method as in claim 1 wherein the step of performing the first reaction includes selecting the first and second times such that one of such times corresponds substantially to a time that the reaction rate for the first analyte reaches a peak during the first reaction.

3. A method as in claim 1 wherein the step of comparing the first and second ratios includes providing the indication if the second ratio differs from the first ratio by a predetermined amount.

4. A method as in claim 1 wherein the step of comparing the first and second ratios includes providing the indication if the second ratio is within a predetermined range of ratios related to the first ratio.

5. A method for providing an indication that a reaction between a sample containing at least a first analyte and a reagent is influenced by the presence of at least a second analyte in the sample also reacting with the reagent but at a rate different from the first analyte comprising the steps of:

performing a first reaction with only the first analyte and the reagent, selecting first and second times for reaction rate measurements such that one of such times corresponds substantially to a time that the reaction rate of the first analyte reaches a peak during the first reaction, measuring first and second reaction rates at the first and second times, respectively, during the first reaction and forming a first ratio between the first and second reaction rates;

performing a second reaction with the sample and the reagent, measuring third and fourth reaction rates at the first and second times, respectively, during the second reaction, and forming a second ratio between the third and fourth reaction rates; and comparing the first ratio and the second ratio and providing the indication if the second ratio differs from the first ratio by a predetermined amount.

6. An apparatus for providing an indication that a reaction between a sample containing at least a first analyte and a reagent is influenced by the presence of at least a second analyte in the sample also reacting with the reagent but at a rate different from the first analyte comprising:

means for performing a first reaction with only a first analyte and a reagent;

means for measuring first and second reaction rates at respective first and second times during the first reaction;

means for forming a first ratio between the first and second reaction rates;

means for performing a second reaction with a sample and the reagent;

means for measuring third and fourth reaction rates at the first and second times, respectively, during the second reaction;

means for forming a second ratio between the third and fourth reaction rates;

means for comparing the first ratio and the second ratio; and means for providing the indication if the second ratio is in a predetermined relationship with the first ratio.

7. An apparatus as in claim 6 wherein the apparatus includes means for fixing the first and second times such that one of such times corresponds substantially to a time that the reaction rate for the first analyte reaches a peak during the first reaction.

8. An apparatus as in claim 6 wherein the apparatus includes means for providing the indication if the second ratio differs from the first ratio by a predetermined amount.

9. An apparatus as in claim 6 wherein the apparatus includes means for providing the indication if the second ratio is within a predetermined range of rate ratios related to the first ratio.

10. An apparatus for providing an indication that a reaction between a sample containing at least a first analyte and a reagent is influenced by the presence of at least a second analyte in the sample also reacting with the reagent but at a rate different from the first analyte comprising:

means for performing a first reaction with only a first analyte and a reagent;

means for fixing first and second times for reaction rate measurements such that one of such times corresponds substantially to a time that the reaction rate of the first analyte reaches a peak during the first reaction;

means for measuring first and second reaction rates at the first and second times, respectively, during the first reaction;

means for forming a first ratio between the first and second reaction rates;

means for performing a second reaction with a sample and the reagent;

means for measuring third and fourth reaction rates at the first and second times, respectively, during the second reaction;

means for forming a second ratio between the third and fourth reaction rates;

means for comparing the first ratio and the second ratio; and means for providing the indication if the second ratio differs from the first ratio by a predetermined amount.

* * * * *